(12) United States Patent
Bovenberg et al.

(10) Patent No.: US 6,368,820 B1
(45) Date of Patent: Apr. 9, 2002

(54) PROCESS FOR THE PREPARATION OF CEPHALOSPORINS USING ACREMONIUM CHRYSOGENUM

(75) Inventors: Roelof Ary Lans Bovenberg, Rotterdam; Dirk Schipper, Delft; Richard Kerkman, Zandvoort, all of (NL)

(73) Assignee: DSM N.V. (NL)

( * ) Notice: Subject to any disclaimer, the term of this patent is extended or adjusted under 35 U.S.C. 154(b) by 0 days.

(21) Appl. No.: 09/230,022

(22) PCT Filed: Jul. 15, 1997

(86) PCT No.: PCT/EP97/03878

§ 371 Date: Jan. 15, 1999

§ 102(e) Date: Jan. 15, 1999

(87) PCT Pub. No.: WO98/02567

PCT Pub. Date: Jan. 22, 1998

(30) Foreign Application Priority Data

Jul. 16, 1996 (EP) .............................................. 96202002

(51) Int. Cl.⁷ ................................................ C12P 35/06

(52) U.S. Cl. ..................................... 435/49; 435/254.11

(58) Field of Search ............................... 435/49, 254.11

(56) References Cited

U.S. PATENT DOCUMENTS 5,559,005 A * 9/1996 Conder et al. ................ 435/47

FOREIGN PATENT DOCUMENTS

| EP | 0 222 462 | 1/2001 |
| EP | 0 532 341 | 1/2001 |
| EP | 0 540 210 | 1/2001 |

OTHER PUBLICATIONS

Crawford et al, Production of Cephalosporin Intermediates by Feeding Adipic Acid to Recombinant *Penicillium chrysogenum* Strains Expression Ring Expansion Activity, Biotechnology, 1995, 13, 58–62.*

Gutierrez et al, Expression of penDE Gene of *Penicillium chrysogenum* Encoding Isopenicillin N Acyltransferase in Cephalosporium Acremonium: Production of Benzylpenicillin by the Transformants, Mol. Gen. Genet. 1991, 225, 56–64.*

Skatrud P.L., Genetic Engineering of Beta–Lactam Antibiotic Biosynthetic Pathways in Filamentous Fungi, Trends in Biotechnology, 1992, 10, 324–329.*

Diez et al, Recombinant *Acremonium chrysogenum* Strains for the Industrial Production of Cephalosporin, Microbiologia Sem., 1996, 12, 359–370.*

Aharonowitz et al., "Penicillin And Cephalosporin Biosynthetic Genes", Ann. Rev. Microbiol. 46 (1992), 461–495.

Alvi et al, "Isolation and Identification of a New Cephem Compound from *Penicillium chrysogenum* Strains Expressing Deacetoxycephalosporin C . . . ", J. Antibiotics 48 (1995), 338–340.

Barredo et al. "Large Amplification of a 35–kb DNA Fragment Carrying Two Penicillin Biosynthetic Genes in High Penicillin Producing Strains of Penicillium . . . ", Curr. Genet. 16(1989), 453–459.

Barredo et al, "Cloning and Characterization of the Acyl–Coenzyme A:6–Aminopenicillanic–Acid–Acyltransferase Gene of *Penicillium chrysogenum*", Genet. 83(1989), 291–300.

Caltrider et al., "Role of Methionine in Cephalosporin Synthesis", (Appl Microbiol. 14(1966), 746–753.

Fierro et al., "The Penicillin Gene Cluster is Amplified in Tandem Repeats Linked by Conserved Hexanucleotide Sequences", Proc. Natl Acad. Sci. 92(1995), 6200–6204.

Gutierrez et al. "The cefG Gene of Cephalosporium Acremonium is Linked to the cefEF Gene and Encodes a Deacetycephalosporin C . . . ", J. Bact. 174(1992), 3056–3064.

Gutierrez et al., "Expression of the penDE gene of *Penicillium chrysogenum* Encoding Isopenicillin N Acyltransferase in Cephalosporium Acremonium:", Mol. Gen. Genet.(1995) 225,56–64.

Hoskins et al. "Gene Disruption of the pcbAB Gene Encoding ACV Synthetase in Cephalosporium Acremonium", Curr. Genet. 18(1990), 523–530.

Yanisch–Perron et al. "Improved M13 Phage Cloning Vectors and Host Strains: Nucleotide Sequences of the M13mp18 and pUS19 Vectors", Gene 33 (1985), 103–119.

Kovacevic et al. "Cloning, Characterization and Expression in *Escherichia coli* of the *Streptomyces clavuligerus* Gene Encoding Deacetoxycephalosproin C . . . ", J. Bact. 171 (1989), 754–760.

Kuck et al. "The 5'–Sequence of the Isopenicillin N–Synthetase Gene (pcbC) from Cephalosporium Acremonium Directs the Expression of the Prokaryotic . . . " Appl. Microbiol. Biotechnol. 31 (1989), 358–365.

Mathison et al. "Cloning, Characterization and use in Strain Improvement of the Cephalosporium Acremonium Gene . . . ", Curr. Genet. 23 (1993), 33–41.

Timberlake, "Cloning and Analysis of Fungal Genes", More Gene Manipulations in Fungi, (1991), 51–79.

Punt et al. "Isolation and Characterization of the Glyceraldehyde–3–Phosphate Dehydrogenase Gene of *Aspergillus nidulans*" Gene 69 1988,49–57.

(List continued on next page.)

Primary Examiner—Nashaat T. Nashed
Assistant Examiner—Malgorzata A. Walicka
(74) Attorney, Agent, or Firm—Morrison & Foerster LLP

(57) ABSTRACT

An improved process for production of an N-acylated cephalosporin is described. The process utilizes an Acremonium strain which has been modified to express an acyl transferase of a filamentous fungus and is selected for production of the N-acylated cephalosporin at a level which is equal to or higher than the production of the corresponding α-aminoadipyl-7-cephalosporins in the strain.

14 Claims, No Drawings

OTHER PUBLICATIONS

Queener et al. "A System for Genetic Transformation of Cephalosporium Acremonium", Microbiology, Am. Soc. for Microbiology (1985), 468–472.

Samson et al. "Cloning and Expression on the Fungal Expandase/Hydroxylase Gene Involved in Cephalosporin Biosynthesis", Bio/Technology vol. 5 (1987), 1027–1214.1.

Skatrud et al. "Efficient Integrative Transformation of Cephalosporium Acremonium", Curr. Genet. 12(1987), 337–348.

Smith et al., "Amplification of the Isopenicillin N Synthetase Gene in a Strain of *Penicillium chrysogenum* Producing High Levels of Penicillin", Mol. Gen. Genet. 216 (1989), 492–497.

Smith et al., "Chromosome Rearrangements in Improved Cephalosporin C–producing Strains of *Acremonium chrysogenum*" Curr. Genet. 19 (1991), 235–237.

Smith et al., "Analysis of Promoter Activity by Transformation of *Acremonium chrysogenum*", Gene 114 (1992), 211–216.

Suominen et al. "High Frequency One–Step Gene Replacement in *Trichoderma reesei*. II Effects of Deletions of Individual Cellulase Genes", Mol. Gen. Genet. 241 (1993), 523–530.

Tischner et al. "Biocatalytic 7–Aminocephalosporanic Acid Production", Enzyme Engineering XI, Eds. Clark and Estell (1992), 502–509.

Van den Hondel et al. "Heterologous Gene Expression in Filamentous Fungi", More Gene Manipulations in Fungi, Eds. Bennett and Lasure (1991), 396–427.

Veenstra et al. "Strain Improvement of *Penicillium chrysogenum* by Recombinant DNA Techniques", J. Biotechnol. 17 (1991), 81–90.

Whitehead et al. "Homologous Transformation of Cephalosporium Acremonium with the Nitrate Reductase–Encoding Gene", Gene 90 (1990), 193–198.

* cited by examiner

PROCESS FOR THE PREPARATION OF CEPHALOSPORINS USING ACREMONIUM CHRYSOGENUM

FIELD OF THE INVENTION

The present invention relates to the field of fermentative production of acylated cephalosporins and their conversion into modified and/or deacylated cephalosporins.

BACKGROUND OF THE INVENTION

β-Lactam antibiotics constitute the most important group of antibiotic compounds, with a long history of clinical use. Among this group, the prominent ones are the penicillins and cephalosporins. These compounds are naturally produced by the filamentous fungi *Penicillium chrysogenum* and *Acremonium chrysogenum*, respectively.

As a result of classical strain improvement techniques, the production levels of the antibiotics in *Penicillium chrysogenum* and *Acremonium chrysogenum* have increased dramatically over the past decades. With the increasing knowledge of the biosynthetic pathways leading to penicillins and cephalosporins, and the advent of recombinant DNA technology, new tools for the improvement of production strains and for the in vivo derivatization of the compounds have become available.

Most enzymes involved in β-lactam biosynthesis have been identified and their corresponding genes been cloned, as can be found in Ingolia and Queener, Med. Res. Rev. 9 (1489), 245–264 (biosynthesis route and enzymes), and Aharonowitz et al., Ann. Rev. Microbiol. 46 (1992), 461–495 (gene cloning).

The first two steps in the biosynthesis of β-lactam compounds are the condensation of the three amino acids L-5-amino-5-carboxypentanoic acid (L-α-aminoadipic acid) (A), L-cysteine (C) and L-valine (V) into the tripeptide LLD-ACV, followed by cyclization of this tripeptide to form isopenicillin N, a penicillin having an a-aminoadipyl side chain. The latter compound contains the typical, β-lactam structure. These first two steps are common in penicillin, cephamycin and cephalosporin producing fungi and bacteria.

In penicillin-producing fungi, like *P. chrysogenum*, the third step involves the exchange of the hydrophilic α-aminoadipyl side chain of isopenicillin N for a hydrophobic, aromatic side chain by the action of the enzyme acyltransferase. The enzymatic exchange reaction mediated by acyltransferase takes place inside a cellular organelle, the microbody, as has been described in EP448180.

In cephalosporin-producing organisms, the third step is the isomerization of isopenicillin N to penicillin N by an epimerase, whereupon the five-membered ring structure characteristic of penicillins is expanded by the enzyme expandase to the six-membered ring characteristic of cephalosporins.

Currently, there is an increasing need for the fermentative production of β-lactam compounds, especially with regard to the cephalosporin intermediates 7-aminodeacetoxycephalosporanic acid (7-ADCA), 7-aminodeacetylcephalosporanic acid (7-ADAC) and 7-aminocephalosporanic acid (7-ACA). Commercial production of these compounds currently requires extensive chemical synthesis steps, which are expensive and noxious to the environment. Fermentative routes to these compounds are described using recombinant *P. chrysogenum* strains (EP 532341 and EP 540210).

*P. chrysogenum* generally is thought to be more suitable than *A. chrysogenum* for the fermentative production of cephalosporin intermediates, mainly because the β-lactam biosynthetic capacity of *P. chrysogenum* is higher than of *A. chrysogenum*, due to extensive strain improvement. For the cephalosporin C producer *A. chrysogenum*, strain improvement has started much later than for *P. chrysogenum*, and additionally no amplification of cephalosporin biosynthetic genes was observed (Smith et al. Curr. Genet. 19 (1991), 235–237), contrary to the penicillin biosynthetic genes which are amplified indeed (Smith et al. Mol. Gen. Genet. 216 (1 989), 492–497; Barredo et al. Curr. Genet. 16 (1989), 453–459; Fierro et al., Proc. Natl. Acad. So;. 92 (1995), 6200–6204).

Recently, it was observed that desacetoxy-cephalosporin was formed in a *P. chrysogenum* strain expressing expandase, implicating that *P. chrysogenum* might contain an epimerase activity as well (Alvi et al., J. Antibiotics 48 (1995), 338–340). This phenomenon diminishes the supposed advantage of *P. chrysogenum* above *A. chrysogenum* as a production organism for the fermentative production of extractable cephalosporins.

*A chrysogenum* strains which express the Penicillium acyltransferase gene have been described (European Patent EP 357119, Gutiérrez et al., Mol. Gen. Genet. 225 (1991), 56–64), but only the production of penicillin G with said recombinant Acremonium strains is disclosed.

Crawford et al. (Bio/Technology 13 (1995), 58–62) suggest the production of adipyl-cephalosporins by feeding adipic acid to an acyltransferase expressing Acremonium strain. However, it is also indicated that this approach would result in a mixture of cephalosporins, with adipyl as well as aminoadipyl side chains, which would present difficulties for downstream processing.

SUMMARY OF THE INVENTION

The present invention discloses a fermentative process for the production of an N-acylated cephalosporin derivative.

Specifically, the process of the invention comprises the fermentation of an Acremonium strain in the presence of a suitable acyl side chain precursor, wherein said Acremonium strain is transformed with an expression cassette comprising an acyltransferase coding sequence and transformants are selected wherein said acyltransferase coding sequence is expressed to a level which leads to a production level of said N-acylated cephalosporin derivative which is similar to or higher than the production level of α-aminoadipyl-7-cephalosporin derivatives.

The process of the invention further comprises the fermentation of an acyltransferase-expressing Acremonium strain in the presence of a suitable acyl side chain precursor, wherein said strain does not express hydroxylase and/or acetyltransferase activity.

The resulting N-acylated cephalosporin derivative is subsequently recovered from the culture fluid.

The N-acylated cephalosporin derivative produced according to the invention is used for the preparation of semisynthetic cephalosporins. Alternatively, the N-acylated cephalosporin derivative is deacylated by chemical or enzymatical means, to produce 7-ADCA, 7-ADAC or 7-ACA.

DETAILED DESCRIPTION OF THE INVENTION

The present invention discloses a fermentative process for the production of N-acylated cephalosporin derivatives, with the proviso that said N-attached acyl group is not the naturally occurring α-aminoadipyl group. Specifically, the present invention discloses a process for the production of N-acylated cephalosporin derivatives using Acremonium as the production organism, wherein Acremonium expresses acyltransferase activity and is cultured in the presence of a suitable N-acyl side chain precursor.

A "suitable" N-acyl side chain precursor is understood to be a side chain precursor which is acceptable to the enzyme acyltransferase as well as to be a side chain precursor which produces a penicillin derivative which is amenable to ring expansion by the enzyme expandase. The α-aminoadipyl side chain present in natural penicillin N-derived cephalosporin compounds is understood not to be covered by the term "suitable" N-acyl side chain.

Examples of such suitable acyl side chain precursors are adipic acid, thiodipropionic acid and carboxymethylthiopropionic acid.

In the process of the invention, an Acremonium strain is used which expresses an acyltransferase gene to a high level. A high expression level is important to minimize the production of α-aminoadipyl-cephalosporin derivative relative to the production of N-acyl-cephalosporin derivative.

To obtain Acremonium strains with a high production level of N-acyl-cephalosporin derivatives relative to the level of α-aminoadipyl-cephalosporins, said strains should have a sufficiently high acyltransferase expression level. A sufficiently high acyltransferase expression level is obtained by using for instance a strong promoter to direct expression of the enzyme. A sufficiently high acyltransferase expression level is further obtained by selecting fungal strains containing multiple copies of an acyltransferase expression cassette.

The Acremonium strain used in the process of the present invention has an acyltransferase expression level which results in a production level of an N-acyl-cephalosporin derivative which is higher than the production level of the α-aminoadipyl-cephalosporin. Preferably, the production level of the N-acyl-cephalosporin derivative is 1.5–3 times higher, more preferably 3–10 times higher, most preferably more than 10 times higher than the production level of the α-aminoadipyl-cephalosporin.

In the process of the invention, the acyltransferase-expressing Acremonium strain is fermented according to common technology. During fermentation, a suitable acyl side chain precursor is fed to the fungal cells. The present invention shows that the acyltransferase ensures the exchange of the α-aminoadipyl side chain in isopenicillin N for said acyl side chain which is fed during fermentation. The resulting acyl-6-APA derivative is subsequently expanded to the acyl-7-ADCA derivative. Depending on the presence of additional enzymes of the cephalosporin biosynthesis pathway, acyl-7-ADCA may be further converted to acyl-7-ADAC or acyl-7-ACA.

In the process of the invention, it is an option to additionally overexpress the gene encoding the enzyme responsible for activation of the side chain precursor, i.e. the appropriate acyl-coA ligase. When using adipic acid as the side chain precursor, said ligase is adipyl-coA ligase.

The use of an Acremonium strain for the fermentative production of N-acylated cephalosporin derivatives has several advantages above the use of a Penicillium strain. Since Acremonium naturally produces cephalosporins, the organism is better equipped than Penicillium to secrete cephalosporin compounds. In addition, β-lactam biosynthetic enzymes from Acremonium may have a longer halflife than those from Penicillium, a difference in stability which is most probably due to differences in the level of endogenous proteolytic enzymes between the two fungi. Moreover, Acremonium strains already possess a reasonable β-lactam production level while the β-lactam biosynthetic genes are still present as single copies. This implicates that amplification of these genes in Acremonium potentially may lead to a substantially higher β-lactam production level.

The use of an acyltransferase-expressing Acremonium strain for the fermentative production of N-acylated cephalosporin derivatives typically results in the formation of an acyl-7-ACA compound. In that regard, a further advantage of Acremonium above Penicillium is applicable. For acyl-7-ACA production with Acremonium, only one enzyme, acyltransferase, needs to be overexpressed, implying that it is relatively easy to obtain a strain with a high expression level of said enzyme, in contrast, for the fermentative production of N-acylated 7-ACA derivatives using *P. chrysogenum*, three different enzyme activities have to be recombinantly expressed in this organism, i.e. an expandase, a hydroxylase, and an acetyltransferase.

To allow for the production of other N-acylated cephalosporin derivatives using Acremonium, such as acyl-7-ADCA or acyl-7-ADAC, a further genetic engineering of an Acremonium strain is necessary. Specifically, for the production of acyl-7-ADCA or acyl-7-ADAC the gene encoding hydroxylase or acetyltransferase, respectively, is inactivated, in addition to introduction of a gene encoding acyltransferase.

In one aspect of the invention, an Acremonium strain expressing an acyltransferase enzyme is prepared by transformation of an Acremonium strain with an expression cassette comprising an acyltransferase coding sequence, wherein said coding sequence may be present as a cDNA or as a genomic DNA fragment. Preferably, the acyltransferase gene originates from Penicillium (the penDE gene) or from *A. nidulans*.

The acyltransferase expression cassette comprises an acyltransferase coding sequence provided with its native 5' and 3' regulatory sequences (transcription and/or translation initiation and termination sequences or with 5' and 3' regulatory sequences originating from a gene other than acyltransferase. Preferably, the acyltransferase coding sequence is provided with 5' and 3' regulatory sequences which give rise to a high level of transcript and corresponding protein.

Examples of suitable 5' and 3' regulatory sequences, i.e. promoters and terminators, providing for recombinant gene expression in filamentous fungus host cells are mentioned in Van den Hondel et al. (in: More Gene Manipulations in Fungi, Eds. Bennett and Lasure (1991), 396–427). Examples of strong promoters functionable in Acremonium are the *A. chrysogenum* isopenicillin N synthase promoter (Skatrud et al. Curr. Genet. 12 (1987), 337–348, Kuck et al. Appl. Microbial. Biotechnol. 31 (1989), 358–365) or the *A. nidulans* glyceraldenyde-3-phosphate promoter (Smith et al. Gene 114 (992), 211–216). Transcriptional terminators can be obtained from the same genes as well.

In a further aspect of the Invention, an acyltransferase-expressing Acremonium strain is used as a host for further transformations, to allow for the production of other N-acylated cephalosporins than acyl-7-ACA.

To obtain an Acremonium strain producing an acyl-7-ADAC, it is necessary to eliminate cephalosporin C acetyltransferase activity in said strain. This is done by inactivation of the gene encoding cephalosporin C acetyltransferase (cefG) in an Acremonium strain, in addition to providing said strain with an acyltransferase expression cassette.

In a similar way, to obtain a strain producing an acyl-7-ADCA, the gene encoding hydroxylase (cefEEF) is inactivated in an Acremonium strain, in addition to providing said strain with an acyltransferase expression cassette. Since in Acremonium hydroxylase and expandase are two activities of the same enzyme molecule, inactivation of the hydroxylase gene simultaneously eliminates expandase activity. Therefore, a gene encoding an expandase with only minor hydroxylase activity, such as the cefE gene from *Streptomyces clavuligerus* (Kovacevic et al. J. Bact. 171 (1989), 754–760) or from *Nocardia lactamdurans*, is simultaneously or subsequently introduced in said Acremonium strain.

Typically, inactivation of a gene is performed by disrupting the coding sequence of the gene to be inactivated.

Inactivation of the cefG or cefEF gene is done using the known cefG gene sequence (Mathison et al. Curr. Genet. 23 (1993), 33–41: Gutierrez et al. J. Bact. 174 (1992), 3056–3064) or cereF gene sequence (Samson et al. Bio/Technology 5 (1987), 1207–1214) and procedures as described by Hoskins et al. (Curr. Genet. 18 (1990), 523–530), Karhunen et 21. (Mol. Gen. Genet. 241 (1993), 515–522) and Suominen et al. (Mol. Gen. Genet. 241 (1993), 523–530).

Briefly, an Acremonium strain is transformed with a so-called disruption cassette. Said disruption cassette comprises a detectable DNA fragment, provided with 5' and 3' flanking sequences which are homologous to the target gene to be inactivated, i.e. the cefG or cefEF gene. Said flanking sequences must be of sufficient length to allow homologous recombination into the target gene. For this purpose, the flanking sequences should comprise at least 1 kb, preferably at least 2 kb and more preferably at least 3 kb target gene sequences. The detectable DNA fragment integrates in the target gene by homologous recombination, either by a single cross-over recombination event, resulting in an insertion of the detectable DNA fragment in the target gene, or by a double cross-over recombination event, resulting in a replacement of target gene sequences by the detectable DNA fragment (in: More Gene Manipulations in Fungi, Eds. Bennett and Lasure (1991), 51–79).

The detectable DNA fragment is a DNA fragment of which the correct integration in the DNA of an Acremonium transformant, i.e. integration in the target gene to be inactivated, is conveniently detectable, e.g. by Polymerase Chain Reaction (PCR) technology and/or Southern hybridisation.

In one embodiment of the invention, the detectable DNA fragment comprises an expression cassette providing for expression of a selection marker.

In another embodiment of the invention, disruption of the cefEF and expression of the cefE gene is achieved in a single transformation event, using a disruption/expression cassette for transformation. Said disruption/expression cassette comprises a disruption cassette directed to the cefEF gene, said cefEF disruption cassette comprising a detectable DNA fragment which is an expression cassette providing for expression of The cefE gene. Next to correct integration of the disruption expression cassette, transformed Acremonium strains are analyzed for expandase expression by checking the nature of the formed N-acyl-cephalosporin derivative.

The desired expression, disruption or disruption/expression cassette is transformed to a suitable Acremonium host strain. Procedures for transformation of *A. chrysogenum* are well known in the art (Queener et al. Microbiology, Am. Soc. for Microbiology (1985), 468–472; Skatruo et al. Curr. Genet. 12 (1987), 337–348; Whitehead et al. Gene 90 (1990), 193–198). To select transformed cells from the nontransformed background, a suitable selection marker is used. Selection markers to be used for selection of fungal transformants are well Known in the art, The selection marker can reside on the same DNA fragment as the desired construct or, alternatively, can reside on a different DNA fragment or vector.

Transformants obtained after the selection procedure are subsequently analyzed for the presence of the desired characteristic, i.e.:

a suitably high production level of the acyl-7-ACA derivative relative to the level of α-aminoadipylcephalosporin compounds. HPLC is a suitable method to discriminate between acyl-7-ACA and α-aminoadipyl-cephalosporin compounds, a correct integration of the disruption or disruption/expression cassette using Southern hybridisation and/or PCR technology, analysis of the nature of the produced N-acylated cephalosporins using HPLC, to check the inactivation of the acetyltransferase and/or hydroxylase gene and/or expression of the re-introduced expandase gene.

The exact order in which the various transformations are performed is not critical to the invention. In a preferred embodiment, an Acremonium strain firstly is transformed with an acyltransferase expression cassette, whereupon a strain with a suitable acyltransferase expression level is selected and used as a host for further transformations.

The present invention further discloses a process for the recovery of an N-acylated cephalosporin derivative, e.g. an acyl-7-ACA derivative, e.g. adipyl-7-ACA, from the fermentation broth of an acyltransferase-expressing Acremonium strain using specific solvents. In this recovery process, the N-acylated cephalosporin derivative is isolated with preference relative to contaminating cephalosporin intermediates having α-aminoadipyl side chains. This recovery process is particularly useful if the level of contaminating α-aminoadipyl cephalosporin derivatives in the fermentation broth is relatively high, e.g. similar to the N-acylated cephalosporin level.

Specifically, adipyl-7-ACA is recovered from the fermentation broth by extracting the broth filtrate with an organic solvent immiscibie with water at a pH of lower than about 4.5 and back-extracting the same with water at a pH between 4 and 10.

The broth is filtered and an organic solvent immiscible with water is added to the filtrate. The pH is adjusted in order to extract adipyl-7-ACA from the aqueous layer. The pH range has to be lower than 4.5; preferably between 4 and 1, more preferably between 2 and 1. In this way, adipyl-7-ACA is separated from many other impurities present in the fermentation broth, especially from the aminoadipyl cephalosporin intermediates. Preferably a smaller volume of organic solvent is used, e.g. half the volume of solvent relative to the volume of aqueous layer, giving a concentrated solution of adipyl-7-ACA, so achieving reduction of the volumetric flow rates. A second possibility is whole broth extraction at a pH of 4 or lower. Preferably the broth is extracted between pH 4 and 1 with an organic solvent immiscible with water.

Any solvent that does not interfere with the cephalosporin molecule can be used. Suitable solvents are, for instance, butyl acetate, ethyl acetate, methyl isobutyl ketone, alcohols like butanol etc. Preferably 1-butanol or isobutanol are used.

Hereafter adipyl-7-ACA is back extracted with water at a pH between 4 and 10, preferably between 6 and 9. Again the final volume can be reduced. The recovery can be carried out at temperatures between 0 and 50° C., and preferably at ambient temperatures.

The above recovery process is also suitable for the preparation of thiodipropionyl- and carboxymethyl-thiopropionyl-7-ACA derivatives, and for the preparation of other N-acylated cephalosporins, like adipyl-, thiodipropionyl-and carboxymethyl-thiopropionyl-7-ADCA derivatives.

The N-acylated cephalosporin derivatives produced by the process of the invention are conveniently used as an intermediate for the chemical synthesis of semisynthetic cephalosporins, since the 7-aminogroup is adequately protected by presence of an appropriate acyl side chain.

Alternatively, the N-acylated cephalosporin derivatives are deacylated in a one-step enzymatical process, using a suitable enzyme, e.g. Pseudomonas SE83 acylase.

Preferably, an immobilized enzyme is used, in order to be able to use the enzyme repeatedly. The methodology for the preparation of such particles and the immobilization of the enzymes have been described extensively in EP 222462. The pH of the aqueous solution has a value of, for example pH 4 to pH 9, at which the degradation reaction of cephalosporin is minimized and the desired conversion with the enzyme is optimized. Thus, the enzyme is added to the aqueous cephalosporin solution while maintaining the pH at the appropriate level by, for instance, adding an inorganic base, such as a potassium hydroxide solution, or applying a cation exchange resin. When the reaction is completed the immobilized enzyme is removed by filtration. Another possibility is the application of the immobilized enzyme in a fixed or fluidized bed column, or using the enzyme in solution and removing the products by membrane filtration. Subsequently, the pH of the aqueous layer is adjusted to 2 to 5. The crystalline deacylated cephalosporin is then filtered off.

The deacylation can also be carried out chemically as known in the prior art, for instance via the formation of an iminochloride side chain, by adding phosphorus pentachloride at a temperature of lower than 10° C. and subsequently isobutanol at ambient temperatures or lower.

The recovery process of the present invention also envisages the option to prepare a deacylated cephalosporin from a mixture of α-aminoadipyl- and an N-acylated cephalosporin derivative, using one and the same process. Both derivatives are isolated from the broth by a column step as described by Tischer et al. (in: Enzyme Engineering XI, Eds. Clark and Estell (1992), 502–509). The mixture of α-aminoadipyl- and N-acylated cephalosporin derivatives is then subjected to a D-amino acid oxidase treatment to convert the α-aminoadipyl-7-cephalosporin derivative to the corresponding glutaryl derivative. The glutaryl as well as the acyl side chains are subsequently removed from the cephalosporin backbone using for instance Pseudomonas SE83 acylase.

EXAMPLE 1

Construction of an Acyltransferase-expressing Acremonium Strain

General Gene Cloning and Gene Transformation Procedures

Common techniques used in gene cloning procedures are used in the present application. These techniques include polymerase chain reactions (PCR), synthetic oligonucleotide synthesis, nucleotide sequence analysis of DNA, enzymatic ligation and restriction of DNA, E. coli vector subcloning, transformation, and transformant selection, isolation and purification of DNA. These techniques are all very well known in the art and adequately described in many references. See for example Sambrook et al., Molecular Cloning, a Laboratory Manual, Cold Siring Harbor, U.S.A. (1989), Innes et al., PCR protocols, a Guide to Methods and Applications, Academic Press (1990), and McPherson et al., PCR, a Practical Approach, IRL Press (1991).

General procedures used in transformation of filamentous fungi and transformant selection include preparation of fungal protoplasts, DNA transfer and protoplast regeneration conditions, transformant purification and characterization. These procedures are all known in the art and very well documented in: Finkelstein and Ball (eds.), Biotechnology of Filamentous Fungi, technology and products, Butterworth-Heinemann (1992); Bennett and Lasure (eds.), More Gene Manipulations in Fungi, Academic Press (1991); Turner, in: Puthler (ed.), Biotechnology, second completely revised edition, VCH (1992).

More specific applications of gene cloning and gene transformation technology to *Acremonium chrysogenum* are well documented in Skatrud (supra), Bennett and Lasure (supra), Finkelstein and Bail (supra), and EP 0 357 119.

Synthetic DNA oligonucleotides are synthesized using a commercial DNA synthesizer (Applied Biosystems, California, U.S.A.) according to the instructions of the manufacturer.

PCR is performed using a commercial automatic PCR apparatus (Perkin Elmer, U.S.A.) and Expand DNA polymerase (Boenringer) according to the instructions of the manufacturer.

Restriction enzymes and other DNA modification enzymes are from ERL (Maryland, U.S.A.) and used according to the instructions of the manufacturer.

*E. Coli* vector pBluescrip: is obtained from Stratagene (California, U.S.A.).

Other chemicals used are all analytical grade, obtained from various suppliers.

DNA nucleotide sequence analysis is performed using an automatic DNA sequence analysis apparatus (Applied Biosystems) based upon detection of sequence-specific fluorescent labelling according to the instructions of the manufacturer.

Culturing of Microorganisms:

*E. coli* XL-1-Blue (Stratagene) and JM 109 (Janisch-Perron et al. Gene 33 (1985), 103–119) are maintained and cultured by using standard *E. coli* culture media (Sambrook, Supra). *A. chrysogenum* ATCC 14553 is grown on lePage-Campbell sporulation medium (per liter: 1 g glucose; 1 g yeast extract; 0.59 g NaCl; 10 g $CaCl_2$; 20 g agar; pH 6.8) for the generation of spores. Solid and liquid media for production of penicillins and cephalosporins are as described by Caltrider and Niss (Appl Microbiol. 14 (1966), 746–753) supplemented with 0.8mg/ml potasiumphenylacetate (PA), for detection of penicillin G, or 0.5–3.0 mg/ml sodiumadipate, for detection of adipylcephalosporins. Cultivation of *A. chrysogenum* for the preparation of protoplasts is done essentially as described by Skatrud et al (supra).

*Micrococcus luteus* is used as an indicator microorganism in bio-assays for penicillins and cephalosporins (Gutierrez et al., Mol. Gen. Genet. (1995) 225, 56–64).

Construction of Acyltransferase Expression Cassette.

Published nucleotide sequences of the *A. nidulans* gpdA gene (Punt et al, Gene 69 1988,49–57) and *P. chrysogenum* penDE gene (Barredo et al, Gene 83 (1989), 291–300) have been used to design synthetic oligonucleotides for PCR amplication of the gpdA promotor and penDE open-reading-frame and transcriptional termination sequences. The sequence of the oligonucleotides is shown in Table 1. The apdA promoter was obtained by PCR as an approximately 0.9 kb fragment containing an unique EcoRI restriction site at the 5' end and an unique NdeI site at the 3' end, by using oligonucleotides 1 and 2 and pAN7-1 plasmid DNA (Punt et al., supra) as template.

TABLE 1

Oligonucleotides used for the construction of an acyltransferase expression cassette.

| | | |
|---|---|---|
| 1 | 5' GAG.CTC.TGT.GAA.TTC.ACA.GTG.ACC.GGT.GAC.TCT.TTC.AGG 3' | (SEQ ID NO:1) |
| 2 | 5' GGG.AGC.CAT.ATG.TGA.TGT.CTG.CTC.AAG.CGG.GGT.AGC.T 3' | (SEQ ID NO:2) |
| 3 | 5' CCC.GCA.GCA.CAT.ATG.CTT.CAC.ATC.CTC.TGT.CAA.GGC 3' | (SEQ ID NO:3) |
| 4 | 5' GGA.CTA.GTG.TCG.ACC.CTG.TCC.ATC.CTG.AAA.GAG.TTG.ATA.TTG.AAG.G 3' | (SEQ ID NO:4) |

In a second PCR the penDE open-reading frame and penDE terminator region was obtained as an approximately 1.8 kb fragment containing an unique NdeI restriction site at the 5' end and a unique SpeI restriction site at the 3' end by using oligonucleotides 3 and 4 and pGJ02 (Veenstra et al. J. Biotechnol. 17 (1991), 81–90; EP 357119) as template.

The PCR products were purified on PCR purification columns (Qiagen) and then digested with restriction enzymes EcoRI and NdeI (0.9 kb gpdA fragment) and NdeI and SpeI (1.8 kb penDE fragment), respectively. The digested PCR fragments were purified and ligated into *E. coli* cloning vector pBluescript (Stratagene) which was digested separately with EcoRI and SpeI. Ligation mixtures were used to transform E. coli XL-1-Blue (Stratagene). Transformants were selected for resistence to ampicillin. Insert containing plasmids (detected by conventional blue/white screening) were isolated from transformants and analysed by restriction enzym analysis and some of them subsequently by nucleotide sequence analysis. The correct assembly of the acyltransferase expression cassette was thus confirmed. The resulting plasmid was designated pGAT. Transformation of *Acremonium chrysogenum* and Selection of Transformants:

The Ca-PEG mediated protoplast transformation is used as described by Skatrud et al (vide supra). pGAT is introduced into *A. chrysogenum* ATCC 14553 by co-transformation with pAN7-1 (Punt et al. vide supra), which confers hygromycin resistance to *A. chrysogenum* (Smith et al. vide supra). Transformants are purified by repeated cultivation on selective medium. Single stable colonies are used for further screening on the presence and expression of acyltransferase. Spores are used to inoculate solid production medium (Caltrider, supra) that contained the penicillin G side chain precursor phenylacetic acid. The capacity of the transformants to produce penicillin G is measured in a bio-assay using *Micrococcus luteus* as indicator strain (Guttierez et al, supra).

Transformants producing large halos, indicative of efficient acyltransferase expression, are used to inoculate liquid medium (Caltrider, supra) supplemented with 0.5–3 mg/ml sodium adipate for production tests. Filtrates of well grown cultures are analysed by HPLC (Crawford et al. supra) for production of adipylcephalosporins and α-aminoadipylcephalosporins. Transformants with favourable adipyl-cephalosporin over α-aminoadipylcephalosporin production are selected and used for production tests at larger scale.

EXAMPLE 2

Recovery of Adipyl-7-ACA from Fermentation Fluid

After filtering of the fermentation broth obtained after fermentation of an acyltransferase-expressing Acremonium transformant in the presence of sodium adipate, about 0.5 volume of 1-butanol is added to the filtrate. The pH value is adjusted to about 1.5 with diluted hydrochloric acid and the mixture is stirred for 5 minutes at room temperature. After separation, the organic layer is either evaporated and further used in the chemical deacylation (Example 3) or back-extracted with 0.5 volume of water of pH 8 and used further in the enzymatic deacylation (Example 4).

EXAMPLE 3

Deacylation of Adipyl-7-ACA

To a mixture of 3 g (8 mmoles) adipyl-7-ACA, 3.5 ml (36 mmoles) of N,N-dimethylaniline, 13 ml of methylene chloride, and 2.6 ml (21 mmoles) of trimethylchlorosilane is added at ambient temperature. After stirring for 30 minutes the reaction mixture is cooled to about –50° C. and 1.8 g (8.5 mmoles) of phosphorus pentachloride is added all at once. The temperature is maintained at –40° C. for two hours and subsequently the reaction mixture is cooled to –65° C. It is then treated with 12 ml (137 mmoles) of isobutanol at such a rate that the temperature does not rise above –40° C. After additional stirring for two hours, the solution is poured in 15 ml of water, and 5 ml of 4.5 N ammonia is added immediately afterwards. The pH is adjusted to 4 by slow addition of solid ammonium bicarbonate. After cooling to 5° C. the mixture is filtered, the crystalline 7-ACA is washed with 5 ml of aqueous acetone (1:1) and isolated.

EXAMPLE 4

Enzymatic Deacylation of Adipyl-7-ACA using Pseudomonas SE83 Acylase

The conversion of adipyl-7-ACA is carried out in a single enzymatic step using an acylase derived from Pseudomonas SE83. The acylase is produced in *E. coli*. Cells are harvested by centrifugation and resuspended in 10 mM phosphate buffer pH 7.4 containing 140 mM NaCl. Subsequently the cells are disrupted by sonification. After removing the cell debris the supernatants containing the acylase activity are collected. Further purification of the acylase is performed by a series of chromatographic steps: (1) on-exchange chromatography on Q-sepharose fast-flow at pH 8.8: (2) hydrophobic interaction chromatography on Phenyl-Sepharose; and 3) gel-permeation chromatography on a Sephacryl S200HR column.

The purified acylase is immobilized onto particles consisting of a mixture of gelatine and chitosan. The particles are treated with glutaraldehyde just before addition of the enzyme.

The conversion of adipyl-7-ACA is carried out in a stirred tank reactor. First the aqueous cephalosporin solution is added to the reactor. Subsequently the temperature of the solution is brought to 30° C. at constant stirring and the pH is fixed at 8 with potassium hydroxide. Then the immobilizes enzyme is added and the conversion starts. During the conversion the pH in the reactor is recorded continuously and kept at 8. The adipic acid which is liberated during the reaction is titrated with KOH. The amount of KOH which is added is integrated and recorded on a flatbed recorder. The conversion is monitored by collecting samples from the reactor which are analyzed for adipyl-7-ACA and 7-ACA by HPLC as described in Example 2.

When the reaction is completed the immobilized enzyme is removed by filtration and the pH of the filtrate is adjusted to about 3. The crystalline 7-ACA is then filtered off.

N-acylated cephalosporin at a level which is equal to or higher than the production level of the corresponding α-aminoadipyl-7-cephalosporins in said strain, and recovering said N-acylated cephalosporin from the culture fluid.

2. The process of claim 1, wherein the production level of said N-acylated cephalosporin is at least 1.5 times higher than that of α-aminoadipyl-7-cephalosporin.

3. The process of claim 1, wherein the production level of said N-acylated cephalosporin is at least 3 times higher than that of α-aminoadipyl-7-cephalosporin.

What is claimed is:

1. A process for the production of an N-acylated cephalosporin comprising the steps of:
   culturing an Acremonium strain in the presence of a cephalosporin N-acyl side chain precursor wherein said Acremonium strain has been transformed with an expression cassette comprising a nucleotide sequence encoding an acyl transferase of a filamentous fungus and is selected for the production of said 4. The process of claim 1, wherein the production level of said N-acylated cephalosporin is at least 10 times higher than that of α-aminoadipyl-7-cephalosporin.

5. The process of claim 1, wherein the N-acyl side chain precursor is selected from the group consisting of adipic acid, thiopropionic acid and carboxymethylthiopropionic acid.

6. The process of claim 1, wherein the Acremonium strain is *A. chrysogenum*.

7. The process of claim 1, wherein the acyl transferase is the product of a penDE gene.

8. The process of claim 7, wherein the penDE gene is that of *Pennicillum chrysogenum*.

9. The process of claim 1, wherein the N-acylated cephalosporin is acyl-7-ACA.

10. The process of claim 1, wherein the N-acylated cephalosporin is acyl-7-ADAC, and said Acremonium strain is further transformed with a disruption cassette for inactivation of the endogenous cefG gene and is selected for correct integration of the disruption cassette in the cefG gene.

11. The process of claim 1, wherein the N-acylated cephalosporin derivative is acyl-7-ADCA, and said Acremonium strain is further transformed with a disruption cassette for inactivation of the endogenous cefEF gene and with an expression cassette for expression of a gene encoding an expandase with only minor hydroxylase activity and is selected for correct integration of the disruption cassette in the cefEF gene, or said Acremonium strain is further transformed with a disruption/expression cassette for inactivation of the endogenous cefEF gene and expression of a gene encoding an expandase with only minor hydroxylase activity and is selected for correct integration of the disruption/expression cassette in the cefEF gene.

12. The process of claim 11, wherein said gene encoding an expandase with only minor hydroxylase activity is the cefE gene of *Streptomyces clavuligerus*, or is the cefE gene of *Nocardia lactamdurans*.

13. The process of claim 1, wherein said N-acylated cephalosporin derivative is recovered as a mixture of an N-acylated cephalosporin and an α-aminoadipyl-7-cephalosporin.

14. The process of claim 1 which further comprises enzymatically deacylating said N-deacylated cephalosporin to obtain an N-deacylated cephalosporin.

* * * * *

SEQUENCE LISTING

```
<160> NUMBER OF SEQ ID NOS: 4

<210> SEQ ID NO 1
<211> LENGTH: 39
<212> TYPE: DNA
<213> ORGANISM: Artificial Sequence
<220> FEATURE:
<223> OTHER INFORMATION: PCR Primer

<400> SEQUENCE: 1
gagctctgtg aattcacagt gaccggtgac tctttcagg                                 39

<210> SEQ ID NO 2
<211> LENGTH: 37
<212> TYPE: DNA
<213> ORGANISM: Artificial Sequence
<220> FEATURE:
<223> OTHER INFORMATION: PCR Primer

<400> SEQUENCE: 2
gggagccata tgtgatgtct gctcaagcgg ggtagct                                   37

<210> SEQ ID NO 3
<211> LENGTH: 36
<212> TYPE: DNA
<213> ORGANISM: Artificial Sequence
<220> FEATURE:
<223> OTHER INFORMATION: PCR Primer

<400> SEQUENCE: 3
cccgcagcac atatgcttca catcctctgt caaggc                                    36

<210> SEQ ID NO 4
<211> LENGTH: 46
<212> TYPE: DNA
<213> ORGANISM: Artificial Sequence
<220> FEATURE:
<223> OTHER INFORMATION: PCR Primer

<400> SEQUENCE: 4
ggactagtgt cgaccctgtc catcctgaaa gagttgatat tgaagg                         46
```